US009662002B2

(12) United States Patent
Liu et al.

(10) Patent No.: US 9,662,002 B2
(45) Date of Patent: May 30, 2017

(54) ENDOSCOPIC PORTAL PROTECTIVE SHIELD ASSEMBLY

(71) Applicants: Kaixuan Liu, Edison, NJ (US); Zsolt Csernatoni, Woodstock, GA (US)

(72) Inventors: Kaixuan Liu, Edison, NJ (US); Zsolt Csernatoni, Woodstock, GA (US)

(73) Assignee: Amendia, Inc., Marietta, GA (US)

( * ) Notice: Subject to any disclaimer, the term of this patent is extended or adjusted under 35 U.S.C. 154(b) by 358 days.

(21) Appl. No.: 14/521,015

(22) Filed: Oct. 22, 2014

(65) Prior Publication Data
US 2016/0007982 A1    Jan. 14, 2016

Related U.S. Application Data

(60) Provisional application No. 62/022,997, filed on Jul. 10, 2014.

(51) Int. Cl.
*A61B 17/02* (2006.01)
*A61B 1/00* (2006.01)
*A61B 1/313* (2006.01)
*A61B 17/34* (2006.01)
*A61B 90/00* (2016.01)

(52) U.S. Cl.
CPC ........ *A61B 1/3135* (2013.01); *A61B 1/00149* (2013.01); *A61B 1/00154* (2013.01); *A61B 17/02* (2013.01); *A61B 17/3421* (2013.01); *A61B 17/0293* (2013.01); *A61B 2017/0256* (2013.01); *A61B 2090/08021* (2016.02)

(58) Field of Classification Search
CPC .............. A61B 17/025; A61B 17/0218; A61B 1/00154; A61B 1/00149; A61B 1/00128; A61B 1/3135; A61B 1/32
See application file for complete search history.

(56) References Cited

U.S. PATENT DOCUMENTS

| | | | |
|---|---|---|---|
| 6,142,931 A * | 11/2000 | Kaji | A61B 1/31 600/102 |
| 6,896,680 B2 | 5/2005 | Michelson | |
| 7,211,085 B2 | 5/2007 | Michelson | |
| 7,377,930 B2 | 5/2008 | Loughran | |
| 7,951,110 B2 | 5/2011 | Bishop et al. | |
| 7,998,143 B2 | 8/2011 | Michelson | |
| 2006/0217754 A1 | 9/2006 | Boehm et al. | |
| 2013/0274557 A1* | 10/2013 | Bowman | A61B 17/0206 600/202 |

FOREIGN PATENT DOCUMENTS

GB        1524528        9/1978

* cited by examiner

*Primary Examiner* — Timothy J Neal
(74) *Attorney, Agent, or Firm* — David L. King

(57) ABSTRACT

An endoscopic portal protective shield assembly has an elongate portal shaft and an elongated protective shield. The elongate portal shaft has a viewing portal. The shaft has a slotted tubular body with interior surfaces. The shaft has a distal end and a proximal end and a slotted opening at the distal end extending partially along the slotted tubular body toward the proximal end. The elongated protective shield has a longitudinal shield body, a proximal end and a distal end. The protective shield is configured to be slid into the slotted opening of the tubular body with an interior portion of the longitudinal shield body being inserted inside the tubular body while maintaining the viewing portal open.

8 Claims, 4 Drawing Sheets

ENDOSCOPIC PORTAL PROTECTIVE SHIELD ASSEMBLY

TECHNICAL FIELD

The present invention relates to endoscopic devices generally, more specifically to an endoscopic portal having a releasable protective shield.

BACKGROUND OF THE INVENTION

When a surgeon is accessing a region to be repaired such as the disc space between adjacent vertebrae, great care must be taken to avoid injury to the exposed nerve root. Endoscopic portal devices provide a means through which the surgeon can observe the tissue in the unobstructed path of the endoscope portal opening. In this way, the surgeon can maneuver the device to see the surgical site.

Minimally invasive spine surgery is an endoscopic procedure that uses specialized video cameras and instruments that are passed through small incisions (less than 2 cm) in the back, chest or abdomen to access the spine and perform the needed surgery.

Most types of minimally invasive surgery rely on a thin telescope-like instrument, called an endoscope, or on a portable X-ray machine, called a fluoroscope, to guide the surgeon while he or she is working. The endoscope is inserted through small incisions in the body. The endoscope is attached to a tiny video camera—smaller than a dime—which projects an internal view of the patient's body onto television screens in the operating room. Small surgical instruments are passed through one or more half-inch incisions, which are later closed with sutures and covered with surgical tape. The fluoroscope is positioned around the patient to give the surgeon the best X-ray views from which to see the anatomy of the spine.

As with any surgical procedure, including minimally invasive spine surgery, there are general risks and procedure-specific risks. The more common general risks of spine surgery include the risk of adverse reactions to the anesthetic, post-operative pneumonia, blood clots in the legs (deep vein thrombosis) that may travel to the lungs (pulmonary embolus), infection at the site of surgery and blood loss during surgery requiring a transfusion. The specific risks of spine surgery include the risk of injury to the nerves or spinal cord resulting in pain or even paralysis, (the estimated risk of paralysis for major spinal reconstructions is somewhere around 1 in 10,000), the instrumentation, if used, breaking, dislodging or irritating the surrounding tissues, and pain from the surgery itself. On rare occasions, during a minimally invasive procedure, the planned surgery cannot be completed and requires either a second trip to the operating room or a conversion from the minimally invasive technique to a full open technique.

Endoscopic spine surgery utilizes dilation technology to create the surgical access through the soft tissue (including skin, subcutaneous fat and muscle/fascia) instead of cutting, in order to minimize access trauma. Beyond the reduced access trauma, the main difference between the endoscopic and the microsurgical microscopic techniques are 2-dimensional versus 3-dimensional vision and an angulated, close-up perspective versus a straight but remote optical perspective.

A number of instrument sets for endoscopic spine surgery are available on the market and they vary considerably in their technical specifications as well as in the indications they are designed for.

It is each individual surgeon's responsibility to ascertain that she or he is using an instrument set that is well suited for the procedure that is being planned. While an endoscopic approach to the spine reduces the (visible) trauma of the surgical approach, this minimal invasiveness comes at a price—reduced and two-dimensional visibility in and limited expandability of the surgical field. The approach and the trajectory chosen in combination with the local anatomy to a large extent define the entry into the spinal canal or the foramen. These anatomical limitations are mostly caused by osseous structures such as the facet joints, the pedicles and the laminae, but also by the exiting nerve root for foraminal approaches and the vertebral arteries for cervical approaches. Together with the characteristics of the optical system (angle of view, magnification, etc.), the size of the working channel and the tools available, this imparts clear limitations as to which places can be viewed and which lesions can be treated safely.

There are burrs, trephines and rongeurs available that allow for the endoscopic resection of bone in order to expand the operative field and to enlarge access.

However, whenever repositioning of instruments through additional access portals, blind reaming with trephines and excessive bony resection is necessary, the advantages of the minimally invasive procedure over a traditional microsurgical approach are reduced and in some cases may even turn into a disadvantage.

A clear surgical strategy and precise targeting are therefore essential. Biplanar fluoroscopy for accurate planning of the approach and for intraoperative control and documentation of instrument position is a prerequisite. When, as it is often the case, tissue modulation technologies such as laser and radiofrequency bipolar devices are utilized in endoscopic spinal surgery, these devices and their potential complications need to be fully understood.

Because of that, there is less interference with the facet joint than with the posterolateral approach, but short pedicles and a large bulging disc can still make the access to the ventral epidural space difficult.

Endoscopic approaches to the cervical spine include, but are not limited to anterior approach and posterior approach.

While traditional microsurgery requires a discectomy, traversing the disc space with an endoscope requires the resection of only a small amount of disc tissue. Sequestrectomy and when required removal of osteophytes is achieved by using a wide range of special instruments including burrs, trephines, microresectors, various types of forceps, drills, hooks and bipolar microelectrodes.

By means of this approach, the foraminal areas and the spinal canal, but not the interpedicular space can be reached with excellent control of the operating field.

More so than in the other segments of the spine, the anterior endoscopic approach facilitates the effective anatomical decompression of the spinal canal and/or the nerve roots (plus in select cases even the vertebral artery) without the requirement to replace the disc by means of a fusion or an arthroplasty. In general, there is no need for a drain or for postoperative immobilization.

The posterior approach is very similar to the traditional microscopic-assisted "keyhole-foraminotomy" approach, just that it is performed using endoscopic equipment and through a smaller approach.

Indications are predominantly lateral soft disc herniations with radicular symptoms, most of which can be addressed with this technique. However, adequate experience in endoscopy and bone resection with drills is necessary due to the risks and consequences of damaging the central nervous system.

After insertion of the working sheath and the endoscope, preparation of the medial aspect of the facet joint and of the ligamentum flavum is performed to clearly identify the anatomical landmarks.

The foraminotomy is begun by bone resection at the medial aspect of the facet joint, resection of the lateral ligamentum flavum.

Then, the lateral edge of the spinal cord and the branching spinal nerve are identified.

Bone resection is necessary in nearly all cases and is performed under direct visual control using drills and bone punches, inserted through the endoscope's working channel.

Bipolar radiofrequency coagulation of the epidural venous plexus and preparation of the spinal nerve under particular attention to possibly separate motor and sensory fascicles comes next.

Depending on the pathology in the individual case, the foraminotomy can be extended towards lateral or craniocaudal.

At the ends of the procedure, direct closure of the skin is done and no drain is required.

While recent studies have shown that endoscopic spinal surgery can be performed with lower complication rates than microsurgical spine surgery, the complications of minimally invasive spine surgery are not necessarily "minimal" when they do occur. Also, the learning curve for endoscopic spinal surgery tends to be flatter and longer than for traditional approaches.

Dural tears, nerve root damage, bleeding and infection, operating on the wrong level or on the wrong side are as real with endoscopic techniques as they are with open techniques.

With thoracic approaches, pneumothorax is also a possibility.

In addition, some injuries may be underestimated or even go unnoticed, such as a dural tear under the low-pressure irrigation of an endoscopic system.

It is an objective of the present invention to further minimize the potential for such complications by providing a unique endoscopic portal made in accordance to the invention as disclosed herein.

SUMMARY OF THE INVENTION

An endoscopic portal protective shield assembly has an elongate portal shaft and an elongated protective shield. The elongate portal shaft has a viewing portal. The shaft has a slotted tubular body with interior surfaces. The shaft has a distal end and a proximal end and a slotted opening at the distal end extending partially along the slotted tubular body toward the proximal end. The elongated protective shield has a longitudinal shield body, a proximal end and a distal end. The protective shield is configured to be slid into the slotted opening of the tubular body with an interior portion of the longitudinal shield body being inserted inside the tubular body while maintaining the viewing portal open. The protective shield body has an interior portion of a cross sectional shape or segment configured to fit against the interior surfaces of the portal shaft adjacent the slotted opening. The proximal end of the protective shield has a shield handle. The shield handle has an opening to align with a shaft body tab opening. The shaft body has a tab at an end of the slot. The tab has the tab opening and when the openings are aligned a fastener can fix the protective shield to the portal shaft. The shield handle opening preferably is threaded to receive the fastener. The fastener, preferably, is fixed to the tab in such a way that it can be tightened or loosened at the convenience of the surgeon.

The shield handle further can include a table arm male adapter configured to be fixed to a female adapter of a table clamp or table arm or otherwise clamped directly to the table. The longitudinal shield body has a rib connecting the interior portion of the shield body interior of the portal shaft to an exterior portion of the shield body. The exterior portion and the interior portion are spaced by the rib to receive and hold the slotted tubular body of the portal shaft adjacent the slotted opening. The distal end of the protective shield extends past the distal end of the portal shaft on assembly. Optionally, the distal end of the protective shield may have a convex exterior and may be tapered to a narrowed rounded tip. The exterior is configured to be positioned to contact a spinal nerve root. Upon insertion, the assembly can be positioned and the portal shaft detached and withdrawn leaving the protective shield in place.

This device provides for a method of treating a spinal injury or defect using an endoscopic portal protective shield assembly. The method includes the steps of making a small incision posteriorly or anteriorly for receiving an endoscopic portal protective shield assembly; inserting the shield assembly; viewing the nerve root, blood vessel or tissue to be shielded; rotating a distal end of the shield to align with and shielding the nerve root, blood vessel or tissue; detaching the protective shield from a tubular body of the endoscopic portal; removing the tubular body leaving the protective shield in aligned position with the nerve root; and completing the surgical repair which may include passing a spinal implant device along the protective shield as a guide to insertion between two adjacent vertebrae and thereafter removing the protective shield and closing the incision.

BRIEF DESCRIPTION OF THE DRAWINGS

The invention will be described by way of example and with reference to the accompanying drawings in which.

DETAILED DESCRIPTION OF THE INVENTION

Figure 1:
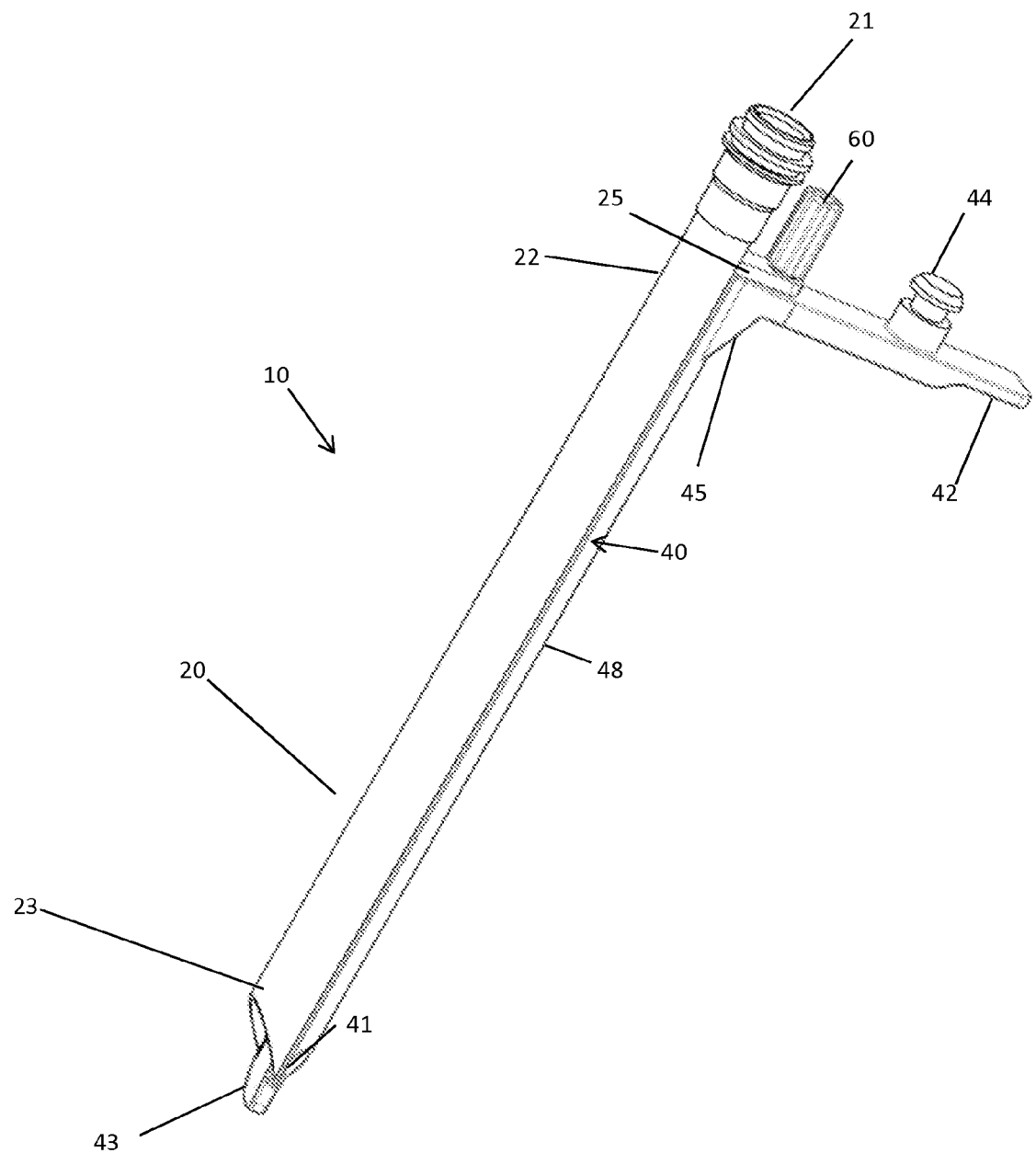
FIG. 1 is a perspective view of the endoscopic protective shield assembly.

With reference to FIGS. 1-4, the endoscopic protective shield assembly 10 of the present invention is illustrated. The endoscopic protective shield assembly 10, as shown, has an elongate portal shaft 20 to which a detachable elongate protective shield 40 has been assembled. As shown, the protective shield 40 has a handle 42 which has been attached to a tab 25 on the portal using a fastener 60. The fastener 60 is affixed in a rotatable fashion about an opening 50 in the tab 25 of the slotted tubular body of the elongated portal shaft. The shield has a threaded opening 52 to which the fastener 60 threadingly engages. The opening 52 being threaded to receive threaded ends of the fastener 60 so that upon assembly, the tubular body 22 of the portal shaft 20 is fixed to the protective shield 40. Preferably, the tubular body 22 can be made of any material; however, it is most desirable that the shaft be made of titanium or stainless steel or other metal. The protective shield body similarly can be made of any material including metals, but is believed preferable to be made of a plastic material or polymer of a medical grade.

Figure 2:
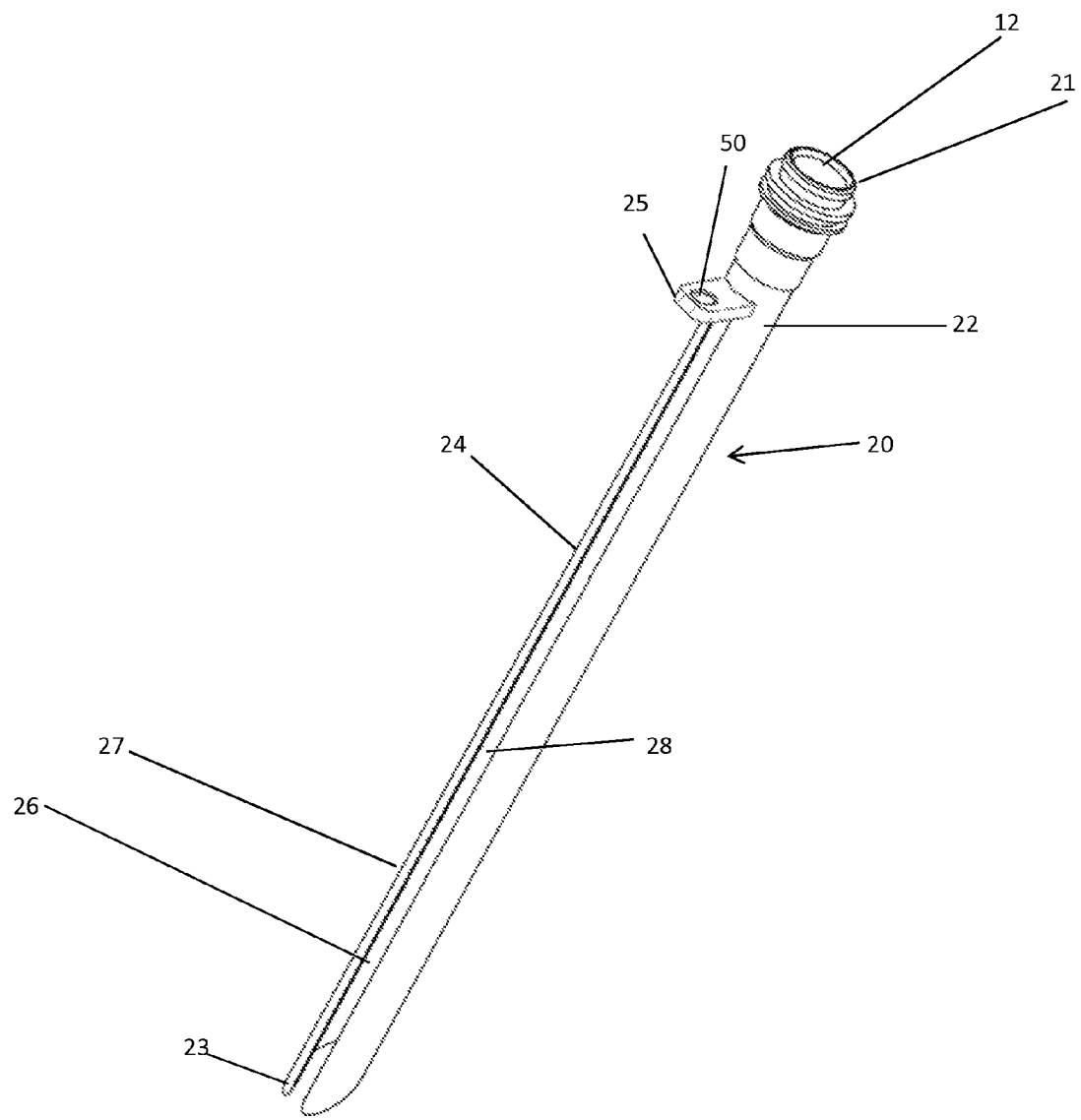
FIG. 2 is a perspective view of the elongate portal shaft.

With reference to FIG. 2, the elongate portal shaft 20 made of the tubular body 22 is shown having an elongated slot 24 that extends from a distal end 23 up to the tab 25 where it terminates approaching near the proximal end 21 of the portal shaft 20. The portal shaft 20 has a viewing port 12, as illustrated, that extends from the proximal end 21 and is completely open to the distal end 23 to allow the surgeon a viewing portal. As further illustrated, the tubular body 22 has a wall having an interior surface 26, adjacent the slot opening 24 are the edges 27 and 28 of the tubular body 22 the viewing port or portal 12 is defined by the interior surface 26 of the wall extending circumferentially between the pair of edges 27, 28.

Figure 3:
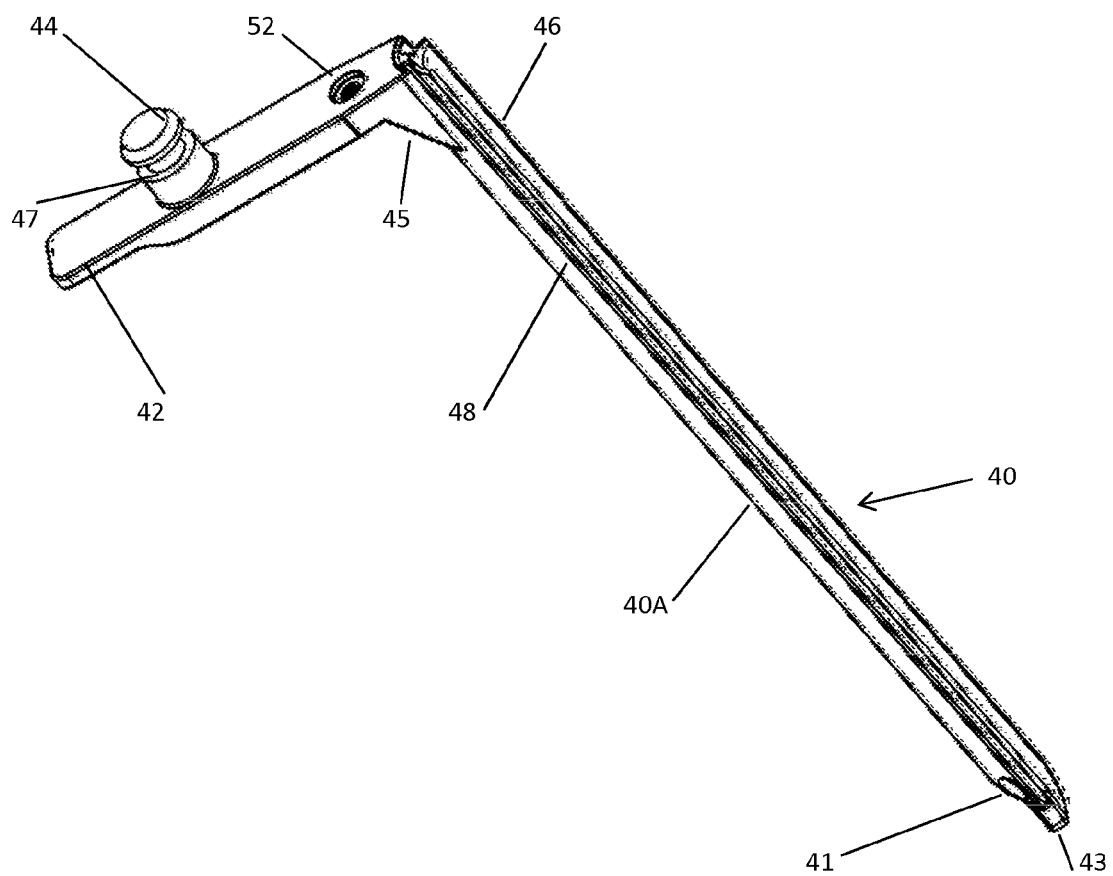
FIG. 3 is a perspective view of the protective shield.
Figure 4:
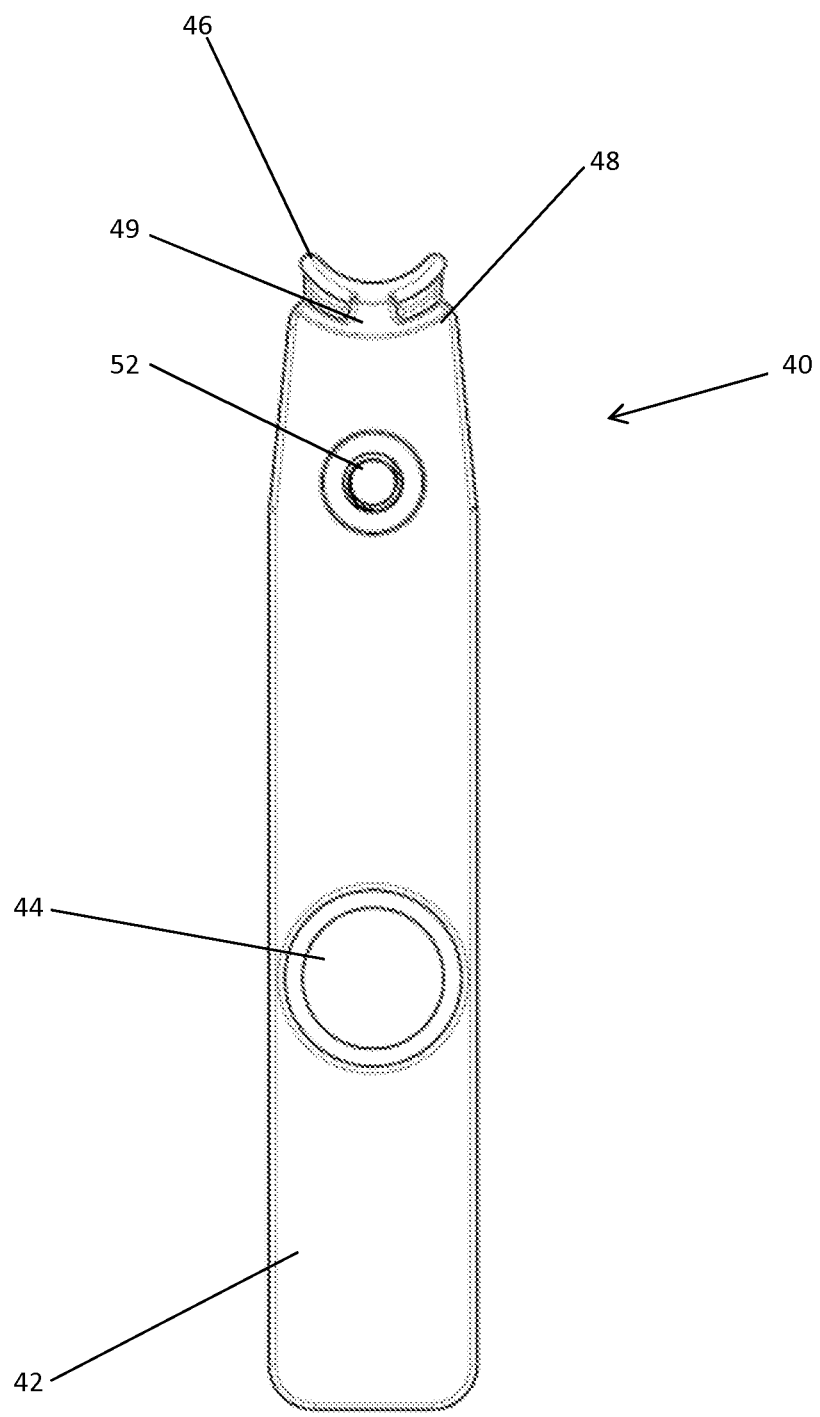
FIG. 4 is a top plan view of the protective shield.

With reference to FIG. 3, the protective shield 40 is illustrated. As shown in FIGS. 3 and 4, the protective shield 40 has an elongated body 40A. The elongated body 40A extends from a handle portion 42 at the proximal end to a distal end 41 extending to a narrowed tip 43. As illustrated, the handle 42 is reinforced and supported by a gusset 45 affixed to the exterior of the shield body 40A. As illustrated, the protective shield 40 as best illustrated in FIG. 3, has an interior portion 46. The interior portion 46 is of a shape that is adapted to fit against an interior surface 26 of the slotted tubular body 22 of the portal shaft 20. The interior body is connected by a rib 49 that connects the interior portion 46 to an exterior portion 48. As illustrated, the exterior portion 48 has a similar shape relative to the interior portion 46 and that allows the elongated protective shield 40 to fit in the slotted opening 24 of the tubular body 22 such that it can slide freely inside its slotted opening 24. As illustrated, when assembled, the interior portion 46 will be inside the tubular body 22 abutting against the interior surface 26. And the rib 49 will position the protective shield 40 such that when it slides up, it fits between the edges 27, 28 of the slotted opening 24 and holds the protective shield 40 between the portions 46, 48 so that it cannot twist or be removed from the portal shaft 20 in any direction, but an axial direction relative to the longitudinal axis of the portal shaft 20. When assembled, the protective shield 40 has a threaded opening 52 on the handle 42 that allows the protective shield 40 to be slid and abutted against the tab 25 and aligned with the opening 50. When the openings are aligned the fastener 60 can be threadingly engaged with the threaded opening 52 to fix the protective shield 40 directly in the slotted opening 24. In this fashion, the endoscopic portal protective shield assembly 10 is complete and the device 10 is ready for use by the surgeon. As shown in FIG. 3, the exemplary device has an arcuate or curved segment interior portion and a similar curvature of the exterior portion as illustrated. This shape is ideally suited for the cylindrical endoscope portal. It is understood these shapes can be any number of optional configurations adapted to fit into and slide into the slot as long as the viewing aperture is left predominantly open. The exemplary figures are simply one design example of numerous options.

As shown, the assembly 10 has the viewing port 12 substantially open and unobstructed by the protective shield 40. The interior portion 46 while being positioned interior of the slotted opening 24 is abutting against the interior surface 26 of the tubular body 22 of the portal shaft 20 in such a way that it lines up against the wall or interior surfaces 26, thus providing minimal obstruction to the viewing port 12 which remains open for the convenience of the surgeon. As illustrated, the distal end 41 of the longitudinal protective shield 40 extends beyond the tubular body 22 at the distal end 23 a sufficient distance to a tip 43 that is rounded. As shown, the distal end 41 that extends beyond the tubular body 22 of the portal shaft 20 can be narrowed tapering down to the tip 43. The distal end 41, upon insertion, allows the surgeon to rotate the assembly 10 such that the tip distal end 41 is rotated to contact an anatomic region or vessel to be protected such as a nerve root or blood vessel and position the distal end between the protected region and the viewing port 12 through which the surgeon may manipulate tools and proceed with any distraction of any material during the surgical repair.

In order to insure that there is no movement of the assembly 10 during the procedure, the handle 42 has an adapter connector 44 attached to it. This adapter connector 44 is designed to be snapped on or otherwise fit along a groove 47 into a table clamp or table arm clamp in such a way that it can fix the assembly's position so it does not move during a surgical procedure. This is important in that the surgeon will be relying on the distal end 41 to maintain its position shielding and protecting the nerve root. Once affixed in position and clamped to the table, the surgeon may then rotate and release the fastener 60 from the attached protective shield 40 and upon doing so may slidingly remove the portal shaft 20 from the assembly 10 leaving only the protective shield 40 in position wherein the surgeon can conduct further procedures if necessary knowing that the nerve root is adequately protected by the pre-positioned protective shield 40. This detachable feature of the protective shield 40 is unique and provides a capability to provide increased confidence for the surgeon during the procedure with the portal shaft 20 in place or when it is completely removed. This assembly 10 provides the surgeon with added convenience and confidence that the nerve will be protected during his procedure by the shield 40.

On insertion of the assembly 10 into the incision anteriorly or posteriorly, the surgeon will first view the surgical field to find the nerve root or blood vessel or tissue to be shielded. Once he locates the nerve root, he will then rotate the entire device 10 in such a way that the distal end aligns with the nerve root, blood vessel or tissue and is positioned between the nerve root, blood vessel or tissue and the viewing field as previously discussed. It is at this point that the surgeon will lock the device to the surgical table to insure that it cannot move and will not move from its protective position in front of the shielded region of the nerve root, blood vessel or tissue.

While the interior portion 46 is shown as an arcuate segment it is appreciated this can be reduced in size slightly and be provided as a flat surface with the primary objective being that the interior portion should not obstruct the viewing port 12. Other alternative configurations such as wedge shaped or other trapezoidal shapes could be applied as well. Similarly, the exterior surface 48 while shown as a rounded exterior surface could be provided as a flat surface as well; however, ideally it is believed that an oval or rounded shape is most convenient for minimizing tissue trauma. It is has been selected for convenience. These and other alternative combinations can be provided without departing from the spirit and scope of the present invention.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. An endoscopic portal protective shield assembly comprising:
   an elongate portal shaft with a viewing portal, the shaft having a slotted tubular body with a wall having an interior surface, a distal end and a proximal end and a pair of edges defining a slotted opening in the distal end extending toward the proximal end partially along the slotted tubular body wherein the viewing portal is defined by the interior surface of the wall extending circumferentially between the pair of edges;
   an elongated protective shield having a longitudinal shield body, a proximal end, a distal end, and wherein the proximal end of the protective shield has a shield handle; and
   wherein the protective shield is configured to be slid into the slotted opening of the tubular body with an interior portion of the longitudinal shield body being positioned interior of the slotted opening inside and abutting against the wall of the tubular body internal of the viewing portal while maintaining the viewing portal open and wherein the shield handle has a handle opening, wherein the slotted tubular body further comprises a tab at the proximal end of the slotted opening, the tab comprises a tab opening, and wherein when the handle opening and the tab opening are aligned a fastener can fix the protective shield to the portal shaft.

2. The endoscopic portal protective shield assembly of claim 1 wherein the interior portion of the longitudinal shield body has a cross sectional shape or segment configured to fit abutting against the wall along the interior surface inside of the shaft adjacent the edges of the slotted opening.

3. The endoscopic portal protective shield assembly of claim 1 wherein the shield handle opening is threaded.

4. The endoscopic portal protective shield assembly of claim 3 wherein the shield handle includes a table arm adapter connector configured to be fixed to a table arm or otherwise clamped directly to a table arm.

5. The endoscopic portal protective shield assembly of claim 1 wherein the longitudinal shield body has a rib connecting the interior portion of the shield body interior of the portal shaft to an exterior portion of the shield body.

6. The endoscopic portal protective shield assembly of claim 5 wherein the exterior portion and the interior portion are spaced by the rib to receive and hold the slotted tubular body of the portal shaft adjacent the slotted opening.

7. The endoscopic portal protective shield assembly of claim 1 wherein the distal end of the protective shield extends past the distal end of the portal shaft on assembly.

8. The endoscopic portal protective shield assembly of claim 1 wherein upon insertion the assembly can be positioned and the portal shaft detached and withdrawn leaving the protective shield in place.

* * * * *